US00PP35024P2

(12) United States Plant Patent
Clark

(10) Patent No.: US PP35,024 P2
(45) Date of Patent: Mar. 7, 2023

(54) ***COLEUS* PLANT NAMED 'UF19-7-4'**

(50) Latin Name: *Coleus scutellarioides*
Varietal Denomination: 'UF19-7-4'

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 10 days.

(21) Appl. No.: 17/803,411

(22) Filed: Jun. 24, 2022

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

(56) References Cited

U.S. PATENT DOCUMENTS

PP33,345 P2 8/2021 Clark

*Primary Examiner* — Susan McCormick Ewoldt
(74) *Attorney, Agent, or Firm* — Katherine Koenig; Koenig IP Works, PLLC

(57) ABSTRACT

A new and distinct cultivar of *Coleus* (*Coleus scutellarioides*) plant named 'UF19-7-4', that was selected because of it has uniform lance-shaped dark yellowish green foliage having a creamy yellow center pattern and a vigorous growth rate. Due to its superior vigor and lateral branching, 'UF19-7-4' does not have to be pinched during production. 'UF19-7-4' has not been observed to produce flowers in any trial conducted. 'UF19-7-4' has long season performance in the landscape until late Fall. 'UF19-7-4' maintains its unique leaf coloration in a broad range of environmental conditions, and it has received superior ratings in both our sun and shade trials. It has a compact and upright growth habit, but it is more highly branched and uniform in shape than most ruffled leaf type *Coleus* plants that have been produced to date, making the plant suitable for use in any part of the garden landscape.

3 Drawing Sheets

Genus and species: *Coleus scutellarioides*.
Cultivar denomination: 'UF19-7-4'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF19-7-4'. The new cultivar 'UF19-7-4' originated from an open pollination conducted in May-November 2018 in Citra, Fla. between the female *Coleus* plant 'UF18-5-13' (unpatented) and an unknown male *Coleus* plant. A single seedling was chosen in May 2019 for further asexual propagation in Gainesville, Fla.

The new cultivar 'UF19-7-4' has been reproduced asexually for over 18 months through meristem tip cuttings and has been found to retain its distinctive characteristics through successive asexual propagations. 'UF19-7-4' was first propagated asexually by meristem tip cuttings in May 2019 in Gainesville, Fla., and has remained true-to-type since that time.

Plant Breeder's Rights for the new cultivar 'UF19-7-4' have not been applied for, and 'UF19-7-4' has not been made publicly available more than one year prior to the filing date of this application.

When compared to the female parent 'UF18-5-13', which has ovate-shaped leaves with crenate margins, the new cultivar 'UF19-7-4' has large lance-shaped leaves that are uniformly lobed, and longer than they are wide. Leaves of 'UF19-7-4' are predominantly dark yellowish green with irregular creamy yellow center patterns that are accentuated in older leaves, whereas leaves of the female parent 'UF18-5-13' are solid chartreuse in color with no patterning and smaller in size. 'UF19-7-4' has a vigorous compact and upright growth habit that is well-branched, whereas 'UF18-5-13' is much less vigorous and more spreading in habit with less lateral branching.

The new cultivar 'UF19-7-4' was selected because: (1) it has unique, lance-shaped leaves with novel color patterning; (2) it is extremely vigorous with much lateral branching, and grows wider than tall, allowing it to fill the landscape with color quickly and reducing or eliminating the need for pinching during production; and (3) it performs well in sun and shade and has excellent vigor to withstand the harsh selection conditions our plants are subjected to in full sun trials in Gainesville, Fla., with long season performance in the landscape until late Fall. 'UF19-7-4' maintains both distinct colors in well-defined zones in shade or sun.

SUMMARY OF THE INVENTION

The new cultivar 'UF19-7-4' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF19-7-4' when grown under normal horticultural practices in Gainesville, Fla. 'UF19-7-4' has the combination of vigorous compact and upright growth habit, excellent heat tolerance, and consistent dark yellowish green leaves having creamy yellow center patterns that are significantly different than other *Coleus* plants. It has superior stability in foliage color in both sun and shade conditions, maintaining stable color in all conditions. It has excellent lateral branching, making it suitable for propagators and producers. 'UF19-7-4' has been observed to have long-season performance in landscape trials in Gainesville, Fla.

DESCRIPTION OF THE FIGURES

This new *Coleus* cultivar 'UF19-7-4' is illustrated by the accompanying photographs, which show the plant's form and foliage. The colors shown are as true as can be reasonably obtained by conventional photographic procedures.

FIG. 2 shows the growth habit, form, and foliage of the claimed plant; and

FIG. 3 shows a close-up view of the foliage of the claimed plant.

DETAILED BOTANICAL DESCRIPTION OF THE CULTIVAR

Figure 1:
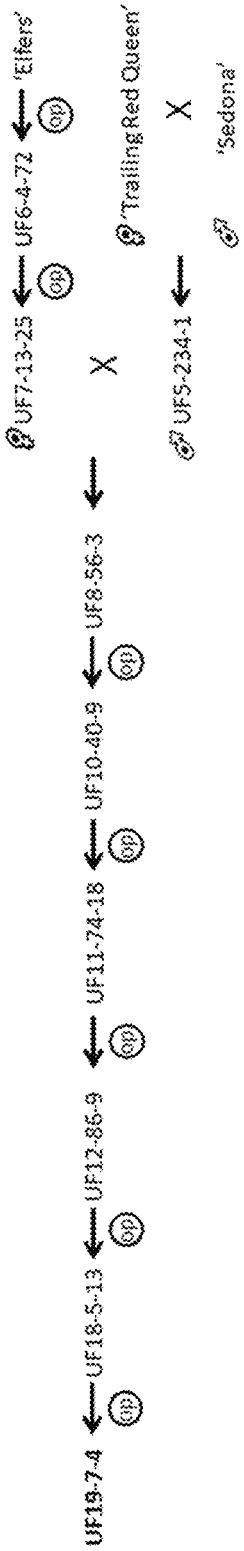
FIG. 1 shows the pedigree of the claimed plant.
Figure 2:
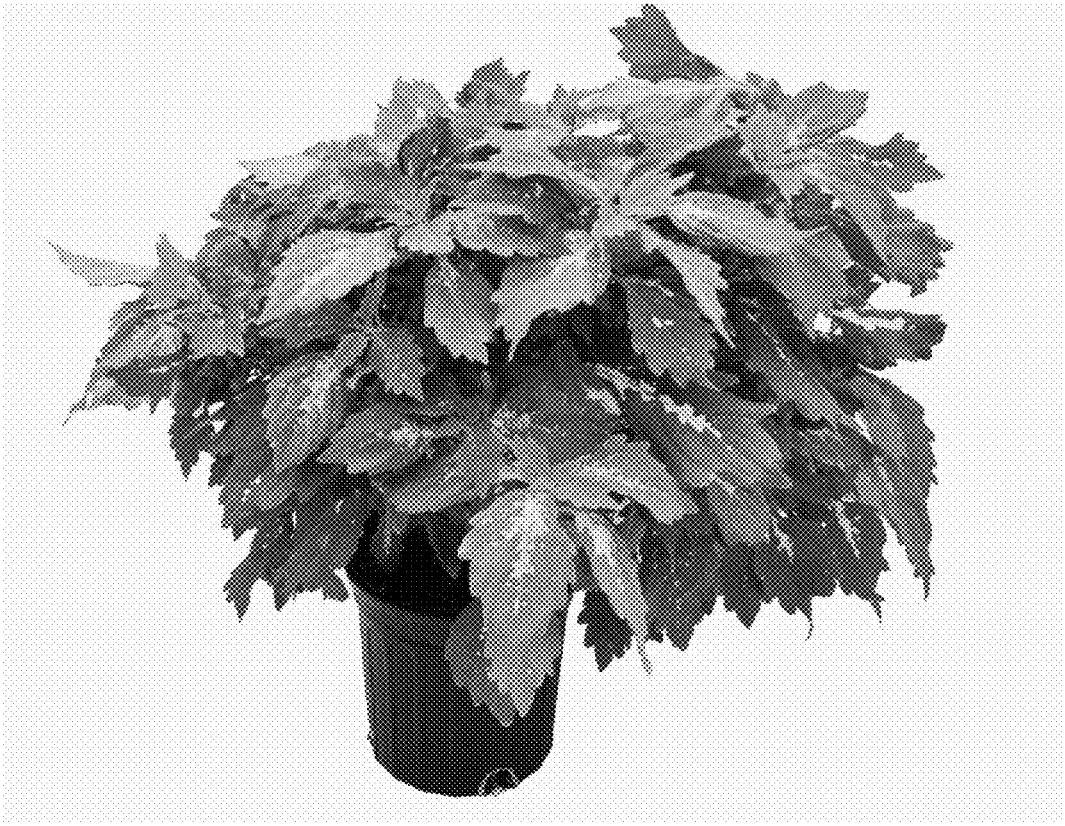
FIGS. 2 and 3 were taken from plants grown nine weeks from unrooted cuttings in September-November 2021 in a glass-covered greenhouse in Gainesville, Fla.
Figure 3:
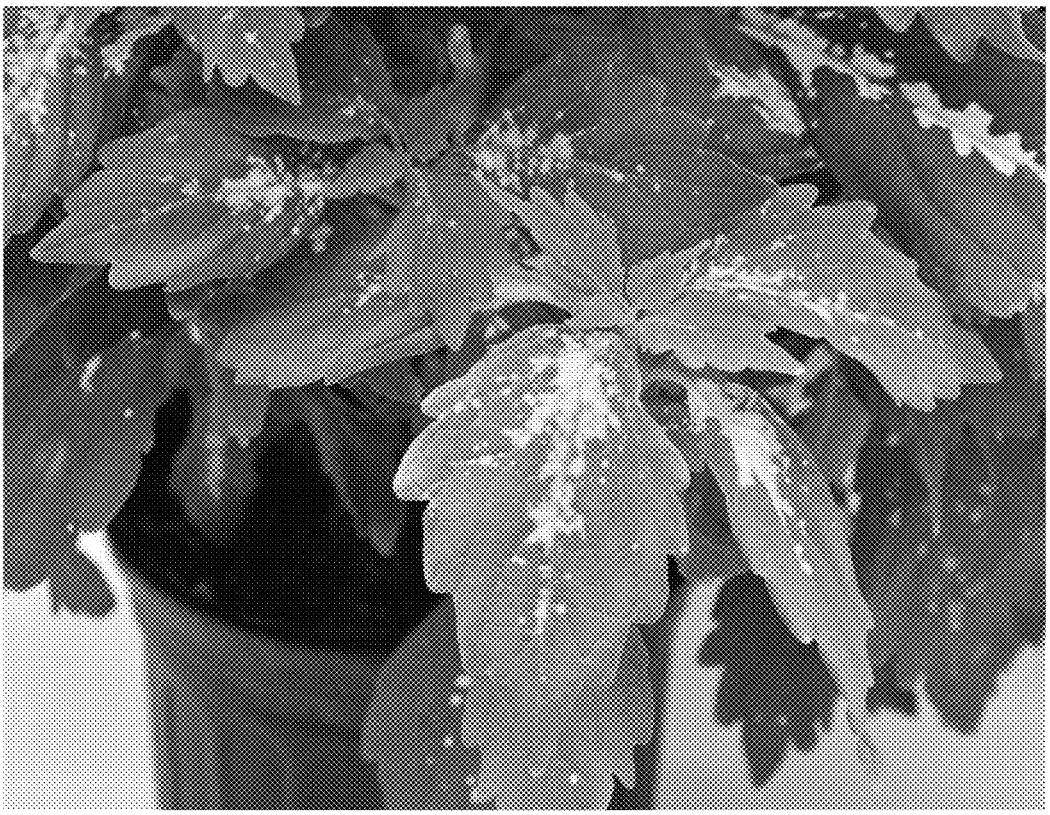

The following detailed description sets forth the distinctive characteristics of the new cultivar 'UF19-7-4'. Foliage color was determined using The Royal Horticultural Society Colour Chart (Royal Horticultural Society, 2007) under full sun conditions in the middle of the day in a glass-covered greenhouse. *Coleus* leaves are rarely one solid color but encompass hues, shades and tints, and color patterns differ from one genotype to another due to varying levels of variegation.

DESCRIPTION OF GROWING CONDITIONS

The detailed description was obtained using nine-week-old plants (from the time the cutting was harvested and stuck) of the new cultivar 'UF19-7-4' pinched once at four weeks after stick and grown in a poly-covered greenhouse in September-November 2021 in Gainesville, Fla.

BOTANICAL DESCRIPTION

Botanical classification:
- *Family*.—Lamiaceae.
- *Botanical name.—Coleus scutellarioides.*
- *Common name.—Coleus.*
- *Cultivar*.—'UF19-7-4'.

Parentage:
- *Female or seed parent*.—'UF18-5-13'.
- *Male or pollen parent*.—Unknown.

Propagation:
- *Type cuttings*.—Vegetative meristem tip cuttings having at least 1 node.
- *Time to initiate roots*.—3-4 days.
- *Time to produce a rooted cutting*.—7-10 days.

Roots:
- *Root description*.—Callus forms in 2-3 days, roots initiate in 3-4 days and become a highly branched cutting in 7-10 days.
- *Rooting habit*.—Fibrous.

Plant description:
- *Growth habit*.—Compact and upright.
- *Plant height* (*from top of soil*).—50-55 cm.
- *Plant width* (*horizontal plant diameter*).—70-75 cm.

Branches:
- *Quantity per plant*.—9-10.
- *Branch color*.—RHS 143A (strong yellow green).
- *Texture*.—Smooth.
- *Pubescence*.—Not present.
- *Stem description*.—Square-shaped stem, 1.2 cm in diameter at the soil line.
- *Branch diameter*.—0.8-0.9 cm at the base of a 53 cm long branch.
- *Branch length*.—50-55 cm.
- *Internode length*.—6-6.5 cm.
- *Anthocyanin*.—Not present.

Foliage description:
- *Quantity of leaves per branch*.—22-24.
- *Arrangement*.—Opposite.
- *Fragrance*.—Not fragrant.
- *Shape*.—Ovate.
- *Length*.—12-13 cm.
- *Width*.—7-9 cm.
- *Apex*.—Broadly acuminate.
- *Base*.—Attenuate.
- *Margin*.—Lobed.
- *Leaf texture*.—Top: Pulverulent. Bottom: Smooth.
- *Pubescence*.—Not present.
- *Venation color*.—Upper surface: RHS 141D (strong yellow green). Lower surface: RHS 141C (strong yellowish green).
- *Venation pattern*.—Upper surface: Reticulate. Lower surface: Reticulate.
- *Color, immature leaf*.—Upper surface, main: RHS 141B (deep yellowish green). Upper surface, center pattern: RHS 150D (light yellow green). Lower surface, main: RHS 139B (moderate yellowish green). Lower surface, center pattern: RHS 150D (light yellow green).
- *Color, mature leaf*.—Upper surface, main: RHS 141B (deep yellowish green). Upper surface, center pattern: RHS 150D (light yellow green). Lower surface, main: RHS 139B (moderate yellowish green). Lower surface, center pattern: RHS 150D (light yellow green).
- *Petiole length*.—4-5 cm.
- *Petiole diameter*.—0.2-0.3 cm.
- *Petiole color*.—RHS 143A (strong yellow green).
- *Petiole texture*.—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Pernonspora lamii*). This pathogen has been observed in stock materials grown closely together in cooler growing seasons.

COMPARISON WITH KNOWN CULTIVARS

Plants of the new *Coleus* cultivar 'UF19-7-4' can be compared to those of 'UF15-4-43' (sold commercially under the trade name LE FREAK™, U.S. Plant Pat. No. 33,345). The center color on the upper surface of mature leaves of 'UF19-7-4' is RHS 150D (light yellow green). In contrast, the center color on the upper surface of mature leaves of 'UF15-4-43' is RHS 187A (dark reddish brown). Additionally, 'UF19-7-4' has a compact and spreading growth habit, whereas 'UF15-4-43' has a spreading growth habit.

What is claimed is:

1. A new and distinct *Coleus scutellarioides* plant named 'UF19-7-4' as shown and described herein.

* * * * *